United States Patent [19]

DeHaan et al.

[11] Patent Number: 4,542,752
[45] Date of Patent: Sep. 24, 1985

[54] IMPLANTABLE DEVICE HAVING POROUS SURFACE WITH CARBON COATING

[75] Inventors: Abel DeHaan, Pembrook Pines; David C. MacGregor, Miami, both of Fla.

[73] Assignee: Cordis Corporation, Miami, Fla.

[21] Appl. No.: 487,460

[22] Filed: Apr. 22, 1983

[51] Int. Cl.⁴ .............................................. A61N 1/04
[52] U.S. Cl. ................................. 128/784; 128/419 P; 29/885
[58] Field of Search ............................... 128/784–786, 128/419 R, 419 P, 635, 419 PG, 303.14, 303.17; 29/885, 855, 874, 875, 880

[56] References Cited

U.S. PATENT DOCUMENTS

| 4,011,861 | 3/1977 | Enger | 128/419 P |
| 4,033,357 | 7/1977 | Helland et al. | 128/419 P |
| 4,052,754 | 10/1977 | Homsy | 128/419 P |
| 4,276,144 | 6/1981 | Hawn et al. | 128/635 |
| 4,280,514 | 7/1981 | MacGregor | 128/419 P |
| 4,440,178 | 4/1984 | Bussard et al. | 128/419 P |

FOREIGN PATENT DOCUMENTS 0072359  8/1981  European Pat. Off. ............ 128/784

*Primary Examiner*—Lee S. Cohen
*Assistant Examiner*—Steven Falk
*Attorney, Agent, or Firm*—Lockwood, Alex, Fitzgibbon & Cummings

[57] ABSTRACT

An implantable device is provided by a process that includes preparing a substrate which has a low impedance carbon coating over a porous substrate. The carbon coating is a carbon lattice formed by plasma depositing a hydrocarbon within an energized gaseous environment. The implantable device is one into which tissue ingrowth is desired, such as electrodes for cardiac and neurostimulation.

27 Claims, 5 Drawing Figures

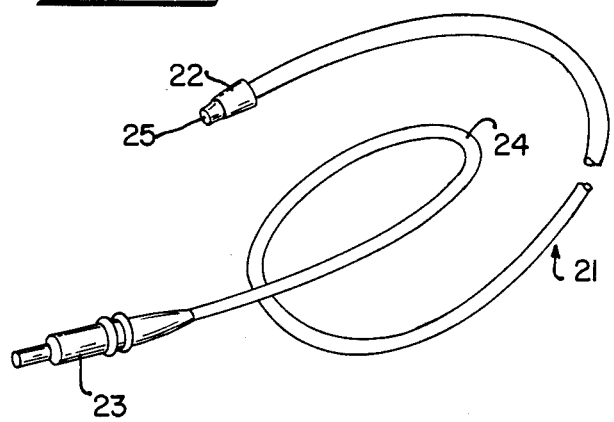
Fig. 1
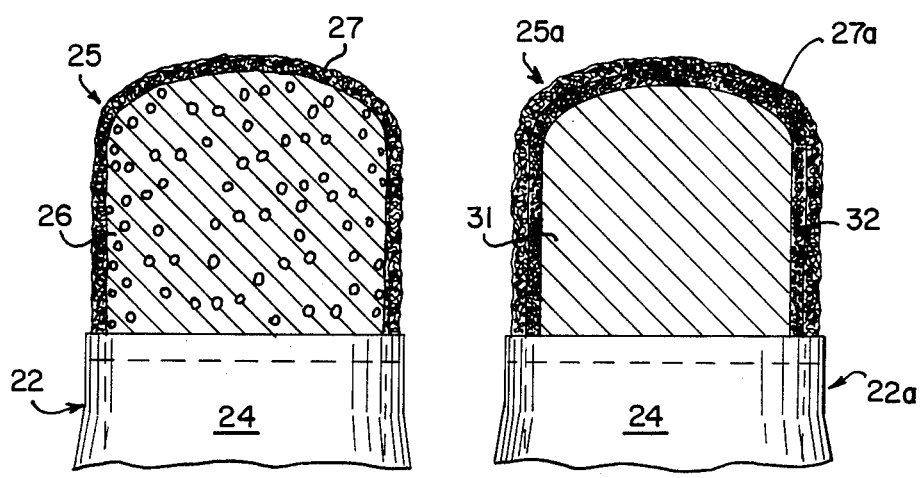
Fig. 2    Fig. 3
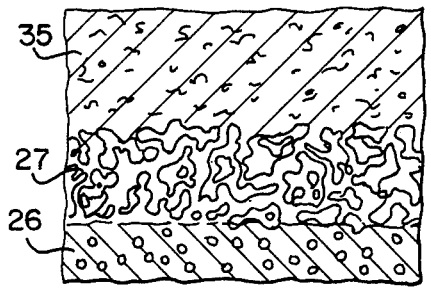  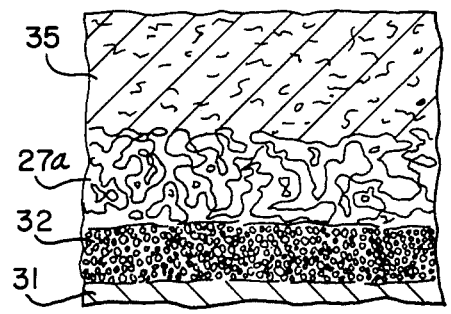
Fig. 4    Fig. 5

IMPLANTABLE DEVICE HAVING POROUS SURFACE WITH CARBON COATING

BACKGROUND AND DESCRIPTION OF THE INVENTION

The present invention generally relates to an implantable device and method for producing same and, more particularly, to an implantable device that has a low impedance carbon coating over a porous substrate. The carbon coating has a lattice structure that is formed onto a porous substrate of an implantable device by a process that includes the plasma deposition of carbon in an energized gaseous environment within which a hydrocarbon is degraded and its carbon is deposited onto the porous substrate.

It has been recognized that in many medical applications, it is desirable to provide a tissue-compatible porous surface. The porous nature of such a surface allows tissue to grow into the porous surface in order to more effectively incorporate the device into the body. Such ingrowth assists in holding the device in place within the body.

Porous platinum surfaces are especially desirable in this regard because of their superior electrical properties; however, because porous platinum coatings tend to be unusually expensive, high-technology alloys have been utilized instead of platinum, and quite successfully, as porous coatings. It would be desirable to provide a relatively inexpensive porous surface that exhibits superior electrical properties and that is of especially enhanced stability and uniformity. Considerations important to stability include resistance to current reversals that might be encountered during use.

Particularly advantageous would be a stable and uniform surface that also maintains an advantageously low polarization impedance. In general, the location of greatest impedance that is experienced with these types of devices is at the interface between the tissue and the outer surface of the device, and attempts and proposals have been made to modify the outer surface of these types of devices in order to improve characteristics of the overall device. Because materials such as carbon have an extremely low electrical impedance, prior activities in this regard include attempts and proposals for using carbon at the interface between such devices and the living tissue into which they are implanted.

Included in such activities have been the utilization of a porous carbon layer over a surface of a shaped, implantable device, appliance or implement. Typically, these porous carbon layers are laid down by sintering or other procedures that include subjecting the surfaces to high temperatures, which often result in a pyrolytic carbon coating that is vitreous or glassy and somewhat amorphous. Additionally, when carbon is laid down by a procedure such as sintering, the carbon is coated in bulk quantities first, and then the bulk carbon layer is sintered or otherwise modified on a scale which is that of a formed coating of substantial thickness. This tends to require very harsh treatment conditions that can result in a final product which is of reduced stability and uniformity.

There is accordingly a need for implantable devices having carbon surfaces that are porous to promote tissue ingrowth thereinto while avoiding harsh treatment of bulk-scale carbon coatings. Also to be avoided is the vitreous condition that high temperature treatments impart to a carbon coating. It is further desirable to simultaneously provide a carbon coating that is unusually uniform in its thickness and pore network even when coated onto uneven surfaces in order to provide a carbon coating that is both thin and uniformly structured, and which will provide minimal impedance and adequate strength under current-transmitting conditions.

Such needs and objectives are accomplished by the present invention by forming a porous carbon coating onto a porous substrate or surface of an implantable device in accordance with a procedure that incorporates plasma deposition and degradation to provide a porous carbon coating that is formed on a generally molecular level in order to impart a porous carbon lattice structure over the porous substrate. The porous carbon plasma deposition procedure includes subjecting the substrate surface to a gaseous environment including a hydrocarbon and energizing that gaseous environment in order to degrade the hydrocarbon, typically in association with polymerization of the hydrocarbon, to form the porous carbon lattice structure.

Accordingly, an object of the present invention is to provide improvements in implantable devices.

Another object of the present invention is to provide an implantable device and process for producing same, which device is suitable for implantation within a living body and for the reception of tissue ingrowth into a carbon coating that is structured by a porous substrate thereunder.

Another object of the present invention is to provide an improved device and process which utilizes plasma polymerization techniques for the formation of a thin carbon coating of low polarization impedance and exceptional stability.

Another object of the present invention is to provide an improved device and process wherein plasma polymerization techniques are tailored in order to deposit a carbon coating on a porous shaped substrate.

Another object of this invention is to provide an improved process and product produced thereby which includes coating a carbon layer under generally flowing conditions whereby a carbon lattice is laid down onto a shaped substrate in a uniform condition that closely conforms to the shape of the substrate, including convoluted surfaces thereof.

Another object of the present invention is an improved method and implantable device that incorporates a carbon coating that is deposited at relatively low temperatures.

Another object of this invention is to provide an improved implantable device that can be used as either an anode or a cathode and that is inert in implantable environments.

Another object of the present invention is an improved process and product produced thereby which provides a porous carbon coating over a variety of porous substrates.

These and other objects, features and advantages of the present invention will be clearly understood through a consideration of the following detailed description.

BRIEF DESCRIPTION OF THE DRAWINGS

In the course of this description, reference will be made to the attached drawings, wherein:

FIG. 1 is a perspective view, partially broken away, of a cardiac pacing lead having a tip assembly that includes an electrode in accordance with the present invention.

FIG. 2 is a cross-section through the end tip assembly of a lead such as that illustrated in FIG. 1, wherein the electrode portion thereof includes a carbon lattice exterior layer over a porous, shaped electrode;

FIG. 3 is a sectional view similar to FIG. 2, wherein the electrode portion thereof has a carbon lattice exterior layer over a porous coating onto a shaped electrode substrate;

FIG. 4 is a schematic illustration of a section through a shaped article in accordance with the present invention, such as the electrode of FIG. 2, after same has been implanted and tissue ingrowth has occurred; and FIG. 5 is a schematic illustration of an enlarged portion of the electrode of FIG. 3, after same has been implanted and tissue ingrowth has occurred.

DESCRIPTION OF THE PARTICULAR EMBODIMENTS

FIG. 1 provides an illustration of the type of device within which this invention is incorporated. The particular device illustrated is an implantable lead, generally designated as 21, which includes a tip assembly 22 and a terminal assembly 23 connected by an elongated conductor member 24, which typically has a protective outer cover and a conductive inner member. The terminal assembly 23 is designed and shaped for use with an implanted cardiac pacemaker. Tip assembly 22 is of the type that provides an exterior, electrically conductive surface. The tip assembly 22 includes a tip member or electrode 25 for contacting the tissue that is to be stimulated by the cardiac pacer.

With more particular reference to the tip assembly 22, further details thereof are illustrated in FIG. 2. Elongated conductor member 24 is securely attached to the tip member or electrode 25 in a suitable manner whereby electrical impulses from the conductor member 24 will be imparted to the tip member or electrode 25 as necessary. The electrode 25 includes a shaped, porous substrate 26 that underlies and gives shape to a porous carbon lattice 27, which porous carbon lattice 27 is formed by a process that includes plasma deposition techniques. Often, the porous substrate 26 will include a plurality of substrate spheres, and the porous carbon lattice 27 conformally coats each such sphere, including its underlying surface. Substrate 26, and any other substrate onto which the carbon is deposited, should be made of a material that is not affected by deposition temperatures.

Regarding FIG. 3, the tip assembly 22a shown therein has an overall structure that can be substantially the same as that of FIG. 2. In this embodiment, a shaped substrate core 31 provides the basic structure for the tip member or electrode 25a. Shaped substrate core 31 typically will not be porous, and it may be a metal such as titanium, a titanium alloy such as a titanium-aluminum-vanadium alloy, platinum, iridium, niobium, cobalt alloys such as Vitallium, paladium, tantalum, vanadium, tungsten, carbon, cobalt, chromium, and alloys of these metals such as Elgiloy, stainless steel or the like. Overlying the shaped substrate core 31 is a thickness of porous material 32, such as porous or sintered titanium, titanium alloys, or Elgiloy, or the like. This structure is particularly useful when it is desired that the substrate core 31 be made of stainless steel or other similar material which is difficult to render porous.

The porous material 32 underlies a porous carbon lattice 27a that is formed by a process that includes plasma deposition techniques. Typically, the porous material 32 will comprise a plurality of spheres, and the porous carbon lattice 27a is shaped by and conformally coats each such sphere including its underlying surface.

FIG. 4 provides a schematic illustration of a portion of an implantable device after tissue ingrowth has occurred, the particular device being one including the shaped, porous substrate 26 and the porous carbon lattice 27 into which the ingrowth of tissue 35 has occurred. In FIG. 5, ingrowth of tissue 35 into the porous carbon lattice 27 is illustrated and further into the thickness of porous material 32 of sintered metal or the like, which overlies the generally non-porous substrate core 31.

With more particular reference to the process according to this invention, the porous shaped substrate has the carbon lattice formed thereover by a procedure that incorporates plasma deposition techniques. As used herein, the term plasma refers to a state that a gas achieves when it is excited to the point of ionization, which is the region in which an active species of the gas is actually formed. Preferred plasma techniques include those of the glow-discharge type wherein a gas is introduced into a vacuum environment within which the shaped substrate is situated, this gaseous environment including energy implemented thereinto. The plasma deposition technique should operate at relatively high power levels and at moderate temperatures.

Provided to the gaseous environment is one or more hydrocarbon, preferably in combination with an inert gas such as argon, helium or neon. Suitable hydrocarbons include those having one or more double bonds including alkenes such as ethylene, propylene, butylene or the like, hydrocarbons having triple bonds such as acetylene, and saturated hydrocarbons such as ethane, propane or the like.

While not being bound by any theory or mechanism, it is believed that the imparted energy polymerizes the hydrocarbon which, under the conditions of the process, is degraded into carbon and hydrogen gas, with the carbon being deposited on the substrate and the hydrogen gas entering the environment. It is believed that the hydrocarbon is excited to form ions and/or free radicals which polymerize. Polymerization may occur in the gaseous or plasma phase, on substrate surfaces, or both. The polymer chains impart a molecular structure to the porous carbon lattice, and the polymer is then degraded into carbon, liberating hydrogen gas, the degradation being effected by the elevated temperatures of the process. A very pure, uniform carbon deposit having an especially non-amorphous, or structured, lattice is formed as the carbon is deposited as a group of atoms, or on a generally molecular level.

Typically, the plasma depositing environment will be of the glow discharge type in an enclosed chamber within which vacuum conditions are developed on the order of between about 0.04 and about 0.065 Torr or higher, typically not greater than about 0.5 Torr. Energy may be implemented thereinto by an energy imparting method and structure, such as a probe for imparting heat and radio frequency (RF) or microwave signals or the like. Gas within the environment is activated by the energy source to such an extent that the gas glows as the energy is supplied thereto under vacuum conditions such that the hydrocarbon at least partially polymerizes and is subsequently degraded. The thickness of the carbon lattice thus formed can be selected by the length of time that the shaped substrate is kept within the environment, which can be on the order of from about 20 minutes to about 3 hours or more. Such thickness will typically be less than 3 mils, preferably less than 1 mil, most preferably on the order of about 0.2 mil.

Within this environment, when the inert gas is present, it assists in controlling the polymerization of the hydrocarbon by acting in the nature of a carrier for transferring and holding energy to assist in the actual polymerization, the inert gas assisting in control of the polymerization by storing excess energy that is developed in the energized hydrocarbon.

The process may include one or more pretreatment steps, whereby the substrate onto which the carbon lattice is to be deposited is first pretreated before the plasma deposition begins. Typically, such pretreatment can be within substantially the same structure and under similar environmental conditions as the plasma deposition procedure itself, although each pretreatment step may proceed for a length of time generally less than that needed for the carbon lattice formation step.

Pretreatment may be in the nature of a plasma cleaning, etching or the like. Initial cleaning can be in conjunction with an inert gas plasma, preferably the same gas to be used in the subsequent deposition step. Etching, which may be the initial step or one subsequent to a cleaning procedure, preferably utilizes a glow discharge plasma that includes a pretreatment agent which is a halogenated methane such as tetrafluoromethane or bromotrifluoromethane.

Such pretreatment steps are especially useful in removing metal oxides that may remain on the surface onto which the carbon lattice is being formed, which metal oxides can increase the impedance of the completed product. Impedance is minimized when the carbon lattice is formed directly onto its substrate, rather than onto a high impedance film such as an oxide layer.

Each pretreatment procedure may be stopped before the deposition plasma is begun. Alternatively, the etching and/or cleaning gas may be continuously blended out of the plasma while the deposition gas is blended into the plasma such that the cleaning and/or etching procedure is continuously and gradually modified into a depositing procedure.

During glow discharge plasma techniques according to this invention, the substrates being coated reach a temperature of between about 300° C. and about 370° C. while deposition proceeds These relatively low temperatures help to avoid the formation of vitreous carbon which is characteristic of a sintered product.

The techniques according to this invention are also especially useful when the carbon lattice is formed over convoluted surfaces, inasmuch as the gaseous procedure readily deposits the carbon matrix into crevices and onto raised members, which allows irregularly shaped devices to be readily coated. The carbon coating is inert in many environments, including implants within living tissue.

One advantage of a low impedance coating is that it substantially eliminates break-down of such a coating on current reversal. Low impedance enhances the life of the battery in a device such as a cardiac pacer. These enhanced electrical properties, especially the low impedance of devices according to this invention, are illustrated by the following examples.

EXAMPLE I

A glow discharge plasma deposition device was used which included a 3-inch outer diameter tubular glass plasma chamber having an inductive radio frequency coupling at about 13.5 MHz. The device also included a metered gas inlet and a metered vacuum hook-up to a vacuum pump, together with a grounded aluminum substrate stage and a shielded thermocouple mounted in such substrate stage.

A cardiac pacing electrode having a porous metal tip that is a porous titanium alloy of 90 weight percent titanium, 6 weight percent aluminum and 4 weight percent vanadium was treated in this apparatus to impart a porous carbon coating according to this invention over this porous metal tip. Several of these porous titanium alloy electrode tips were first pretreated by plasma etching in a carbon tetrafluoride plasma. These electrode substrates and the stage were heated to about 335° C. by the radio frequency coupling inductive heating that is accomplished by the device. The flow rate of the carbon tetrafluoride was 2.0 cubic centimeters per minute at standard temperature and pressure (Sccm). The pressure of the carbon tetrafluoride plasma was maintained between 40 and 47 $\mu$Hg, and the plasma was run for between one hour and two and one-half hours. This plasma etching removed metal oxides from the surface of the porous titanium alloy substrate.

Next, a low-impedance, conductive porous carbon coating was deposited onto a plasma etched porous electrode within a structure substantially identical to that used during etching. A plasma of argon gas containing about 18 percent propylene at a flow rate of about 7.7 to 7.8 Sccm and a pressure of about 50 $\mu$Hg provided a plasma flow that was run for between 35 and 150 minutes, while the substrates and their stage were maintained at a temperature of about 340° C.

The carbon coated pacing electrodes thus prepared were subjected to various tests and analyses. Adhesion was tested by directing a jet of compressed gas onto and by applying "Scotch" tape to the carbon coating. Neither test removed any of the coating. While black powder could be manually rubbed off sections of the carbon coating, the coating itself did not rub off. The linear polarization of the pacing electrode is excellent, the electrode polarization being between 100 and 225 mV through about 2 msec. The polarization impedance was about 45 to 90 ohms. A scratch in the carbon coating does not substantially change the polarization impedance. Electrode recovery is exceptionally fast, recovery being substantially complete at about 7 msec. from the polarization potential. The electrodes prepared according to this invention have an exceptionally low impedance which is not substantially affected by simulated pacing for one month. The impedance at about −0.75 V was about 480 ohms for one of the electrodes tested and about 543 ohms for another tested electrode during the cathodic sweep of cyclic voltammetry tests from −1.0 to +1.0 V versus a calomel reference electrode.

Comparison A

The preceeding work of Example I in accordance with this invention was essentially repeated, except the substrate was a smooth, round-tipped, non-porous titanium electrode. This non-porous substrate was satisfactorily etched and the conductive carbon was deposited thereon. Adhesion of the conductive carbon was inferior to that of Example I. The carbon coating was easily removed by a tweezers.

Comparison B

A commercially available pacing electrode having an activated carbon tip was found to have a polarization potential and a polarization impedance that are very similar to those of the pacing electrodes prepared in accordance with Example I. Impedance measurements taken in accordance with cyclic voltammetry was higher than that of the pacing electrodes of Example I, such impedance at −0.75 V being about 949 ohms.

Comparison C

A known pacing electrode having a relatively expensive porous platinum tip was tested and exhibited an electrode recovery time slower than that of the Example I electrodes. Recovery time from the polarization potential for the porous platinum electrode was substantially completed at approximately 300 msec., the polarization being approximately 500 mV. The polarization impedance was 203 ohms over about a 2 msec. pulse.

EXAMPLE II

Porous Elgiloy metal alloy electrodes of various designs were plasma cleaned in an argon gas plasma within an apparatus in accordance with Example I. The radio frequency coupling inductively heated the substrate and their stage to between 300 and 370° C., and the argon flow rate was 2.5 Sccm at a pressure of between 50 and 60 µHg. Plasma cleaning proceeded for 2-½ hours. Each electrode was then plasma etched in a tetrafluoromethane plasma and then carbon coated in a manner consistent with that followed in Example I.

The carbon coating of these electrodes passed the compressed gas, Scotch tape, and rubbing adhesion tests. In linear polarization tests, these pacer electrodes exhibited a polarization potential of 433 mV over about 2 msec. The polarization impedance was about 177 ohms. The carbon coated electrode impedance was not substantially affected by simulated pacing for one month.

It will be understood that the embodiments of the present invention which have been described are merely illustrative of a few of the applications of the principals of the present invention. Numerous modifications may be made by those skilled in the art without departing from the true spirit and scope of the invention.

What is claimed is:

1. A device or appliance that is implantable in organic tissue, comprising:
   an electrically conductive shaped element having a shaped substrate member that is electrically conductive and porous to provide a convoluted surface for enhancing organic tissue ingrowth thereinto; and
   a low impedance carbon coating over said electrically conductive porous shaped substrate member, said low impedance carbon coating having a carbon lattice structure, said carbon lattice structure being a plasma deposit of carbon laid down on a generally molecular level, said carbon lattice structure providing a porous surface that had been substantially shaped by and conformally coated onto said convoluted surface of the electrically conductive porous shaped substrate member; wherein said low impedance carbon coating lattice structure plasma deposit having been laid down by subjecting said electrically conductive porous shaped substrate member to a gaseous environment including a hydrocarbon and energizing the gaseous environment to degrade the hydrocarbon into carbon and hydrogen and to form said carbon lattice structure.

2. The implantable device or appliance according to claim 1, wherein said porous shaped substrate member is a porous metal structure.

3. The implantable device or appliance according to claim 1, wherein said porous shaped substrate member is a porous sintered metal.

4. The implantable device or appliance according to claim 1, wherein said shaped substrate member includes a sintered metal as the porous convoluted surface thereof, said sintered metal underlying said low impedance carbon coating lattice structure and overlying a shaped substrate core.

5. The implantable device or appliance according to claim 1, wherein said porous shaped substrate member includes a plurality of metal spheres.

6. An electrically conductive shaped element as a portion of a device or appliance that is implantable in organic tissue, comprising:
   a shaped substrate member that is electrically conductive and porous to provide a convoluted surface for enhancing organic tissue ingrowth thereinto; and
   a low impedance carbon coating over said electrically conductive porous shaped substrate member, said low impedance carbon coating having a carbon lattice structure, said carbon lattice structure being a plasma deposit of carbon laid down on a generally molecular level, said carbon lattice structure providing a porous surface that had been substantially shaped by and conformally coated onto said convoluted surface of the electrically conductive porous shaped substrate member; wherein
   said low impedance carbon coating lattice structure plasma deposit having been laid down by subjecting said electrically conductive porous shaped substrate member to a gaseous environment including a hydrocarbon and energizing the gaseous environment to degrade the hydrocarbon into carbon and hydrogen and to form said carbon lattice structure.

7. The shaped element according to claim 6, wherein said porous shaped substrate member has a porous metal surface.

8. The shaped element according to claim 6, wherein said shaped substrate member includes a sintered metal as the porous convoluted surface thereof, said sintered metal underlying said low impedance carbon coating lattice structure and overlying a shaped substrate core.

9. The shaped element according to claim 6, wherein said porous shaped substrate member includes a plurality of metal spheres.

10. A process for making a device or appliance that is implantable in organic tissue and that has a convoluted surface for enhancing organic tissue ingrowth thereinto, comprising:
   providing an electrically conductive shaped element having a shaped substrate member that is electrically conductive and porous, thereby providing the covoluted surface;
   plasma depositing a carbon lattice structure onto said porous convoluted surface of the electrically conductive shaped substrate member, said carbon lattice structure being a low impedance carbon coating onto said convoluted surface that is laid down on a generally molecular level, said plasma depositing including the steps of:

subjecting said porous convoluted surface of the electrically conductive porous shaped substrate member to a gaseous environment including a hydrocarbon; and energizing the gaseous environment to degrade the hydrocarbon into carbon and hydrogen to form the carbon lattice structure coated onto said porous convoluted surface of the electrically conductive porous shaped substrate member, wherein said energizing step includes forming the carbon lattice structure as a porous surface by conforming the carbon into a carbon lattice structure that is substantially shaped by and conformally coated onto said porous convoluted surface.

11. The process of claim 10, wherein said plasma depositing includes a glow discharge procedure.

12. The process of claim 10, wherein the porous convoluted surface is formed by metal sintering.

13. The process of claim 10, wherein the gaseous environment includes an alkene.

14. The process of claim 10, wherein the gaseous environment includes an inert gas.

15. The process of claim 10, wherein the gaseous environment includes a hydrocarbon selected from the group consisting of hydrocarbons having one or more double bonds, hydrocarbons having triple bonds, and saturated hydrocarbons.

16. The process of claim 10, wherein the gaseous environment includes a hydrocarbon having one or more double bonds.

17. The process of claim 10, further including pretreating the porous convoluted surface by plasma techniques, said pretreating step being before said plasma depositing of the carbon lattice structure.

18. The process of claim 10, wherein said energizing step includes polymerizing the hydrocarbon.

19. The process of claim 10, further including pretreating the porous convoluted surface by subjecting the porous convoluted surface to a glow discharge gaseous environment including a pretreatment agent and energizing the pretreatment gaseous environment.

20. The process of claim 10, further including pretreating the porous convoluted surface by subjecting the porous convoluted surface to a glow discharge gaseous environment including a tetrahalogenated alkane and energizing the pretreatment gaseous environment.

21. The process of claim 10, further including pretreating the porous convoluted surface by subjecting the porous convoluted surface to a glow discharge gaseous environment including a tetrafluoromethane or bromotrifluoromethane and energizing the pretreatment gaseous environment.

22. The process of claim 10, further including pretreating the porous convoluted surface within a gaseous environment including an inert gas and a pretreatment agent.

23. The process of claim 10, further including a pretreatment step which is a plasma cleaning that includes subjecting the porous convoluted surface to an inert gas environment and energizing that environment.

24. The process of claim 10, further including a plurality of pretreatment steps including a plasma cleaning step that includes subjecting the porous convoluted surface to an inert gas environment and energizing that environment, followed by a further pretreatment step that is a plasma etching step utilizing a halogenated alkane within a gaseous environment.

25. The process of claim 10, wherein said gaseous environment includes an inert gas added to a vacuum environment.

26. The process of claim 10, wherein said gaseous environment is within an enclosed chamber.

27. The process of claim 10, wherein said energizing step includes imparting radio frequency energy which raises the temperature of the substrate to between about 300° and 370° C.

* * * * *